United States Patent
Hoshina et al.

(10) Patent No.: US 10,505,177 B2
(45) Date of Patent: Dec. 10, 2019

(54) NONAQUEOUS ELECTROLYTE BATTERY ELECTRODE, NONAQUEOUS ELECTROLYTE BATTERY, AND BATTERY PACK

(71) Applicant: Kabushiki Kaisha Toshiba, Minato-ku (JP)

(72) Inventors: Keigo Hoshina, Yokohama (JP); Wen Zhang, Sagamihara (JP); Yusuke Namiki, Kawasaki (JP); Yoshiyuki Isozaki, Nerima (JP); Norio Takami, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/689,583

(22) Filed: Aug. 29, 2017

(65) Prior Publication Data

US 2017/0365842 A1  Dec. 21, 2017

Related U.S. Application Data

(63) Continuation of application No. PCT/JP2015/077103, filed on Sep. 25, 2015.

(51) Int. Cl.
*H01M 4/131* (2010.01)
*H01M 4/62* (2006.01)
(Continued)

(52) U.S. Cl.
CPC .......... *H01M 4/131* (2013.01); *H01M 4/621* (2013.01); *H01M 10/0525* (2013.01);
(Continued)

(58) Field of Classification Search
CPC .. H01M 4/131; H01M 4/621; H01M 10/0525; H01M 4/5825; H01M 2004/027;
(Continued)

(56) References Cited

U.S. PATENT DOCUMENTS

2002/0061440 A1  5/2002  Suzuki et al.
2006/0127773 A1*  6/2006  Kawakami ............ H01M 4/134
                                                            429/245
(Continued)

FOREIGN PATENT DOCUMENTS

EP   2 120 279 A1   11/2009
JP   2002-75458     3/2002
(Continued)

OTHER PUBLICATIONS

International Search Report dated Dec. 15, 2015 in PCT/JP2015/077103, filed on Sep. 25, 2015 (with English Translation).
(Continued)

*Primary Examiner* — Gary D Harris
(74) *Attorney, Agent, or Firm* — Oblon, McClelland, Maier & Neustadt, L.L.P.

(57) ABSTRACT

A nonaqueous electrolyte battery electrode according to an embodiment includes a current collector and a mixed layer formed on one surface or both surfaces of the current collector. The mixed layer includes an active material and a binding agent. The ratio $I_2/I_1$ of the highest peak intensity $I_2$ in peaks appearing in the wavelength range of 1400 to 1480 $cm^{-1}$ to the highest peak intensity $I_1$ in peaks appearing in the wavelength range of 2200 to 2280 $cm^{-1}$ is 10 or more and 20 or less in an infrared absorption spectrum measured according to a total reflection measurement method. Alternatively, in the mixed layer, the ratio $I_3/I_2$ of the highest peak intensity $I_3$ in peaks appearing in the wavelength range of 1650 to 1850 $cm^{-1}$ to the highest peak intensity $I_2$ in peaks appearing in the wavelength range of 1400 to 1480 $cm^{-1}$ is 0.1 or more and 0.8 or less in an infrared absorption spectrum measured according to a total reflection measurement method.

26 Claims, 5 Drawing Sheets

(51) Int. Cl.
*H01M 10/0525* (2010.01)
*C07C 255/08* (2006.01)
*G01N 21/35* (2014.01)
*H01M 4/02* (2006.01)

(52) U.S. Cl.
CPC .... *C07C 255/08* (2013.01); *G01N 2021/3595* (2013.01); *H01M 2004/027* (2013.01)

(58) Field of Classification Search
CPC ....... H01M 2004/021; H01M 10/0567; H01M 4/525; H01M 4/505; G01N 21/552; G01N 2021/3595; C07C 255/08
USPC ..................................................... 429/231.5
See application file for complete search history.

(56) References Cited

U.S. PATENT DOCUMENTS

| | | | | |
|---|---|---|---|---|
| 2010/0015514 | A1* | 1/2010 | Miyagi | ................ H01M 4/131 429/129 |
| 2011/0318655 | A1 | 12/2011 | Kawasoe et al. | |
| 2012/0308890 | A1 | 12/2012 | Okuda et al. | |
| 2014/0023935 | A1 | 1/2014 | Noguchi et al. | |
| 2014/0041209 | A1 | 2/2014 | Minami et al. | |
| 2014/0287285 | A1 | 9/2014 | Inagaki et al. | |
| 2015/0079438 | A1 | 3/2015 | Inagaki et al. | |
| 2015/0194668 | A1 | 7/2015 | Ueda et al. | |
| 2016/0218390 | A1 | 7/2016 | Yamada et al. | |
| 2017/0077550 | A1* | 3/2017 | Nishie | ................ H01M 10/052 |

FOREIGN PATENT DOCUMENTS

| | | |
|---|---|---|
| JP | 2012-9370 | 1/2012 |
| JP | 2012-248441 | 12/2012 |
| JP | 2014-35949 | 2/2014 |
| JP | 2015-60713 | 3/2015 |
| WO | WO 2012/141301 A1 | 10/2012 |
| WO | WO 2014/046144 A1 | 3/2014 |
| WO | WO 2015/045386 A1 | 4/2015 |
| WO | WO 2015/133097 A1 | 9/2015 |

OTHER PUBLICATIONS

Written Opinion dated Dec. 15, 2015 in PCT/JP2015/077103, filed on Sep. 25, 2015.

Office Action dated Feb. 20, 2019, in European Patent Application No. 15904727.3, filed Sep. 25, 2015.

* cited by examiner

NONAQUEOUS ELECTROLYTE BATTERY ELECTRODE, NONAQUEOUS ELECTROLYTE BATTERY, AND BATTERY PACK

FIELD

Embodiments described herein relate to a nonaqueous electrolyte battery electrode, a nonaqueous electrolyte battery, and a battery pack.

BACKGROUND

Nonaqueous electrolyte batteries in which charging and discharging are performed when lithium ions move between a negative electrode and a positive electrode have been actively studied as high-energy-density secondary batteries.

In addition to applications as a power supply for a small electronic device, nonaqueous electrolyte batteries are also expected to be used as a medium and large power supply for automotive applications and stationary applications. Life characteristics and high safety are required for such medium and large applications. Furthermore, charging and discharging characteristics under a high-temperature or low-temperature environment are also required.

It is required that oxidation and reductive decomposition do not proceed for a nonaqueous electrolyte used for a nonaqueous electrolyte battery which has excellent life characteristics and charging and discharging characteristics under high-temperature or low-temperature environments. As a method of preventing oxidation of a nonaqueous electrolyte, an electrolyte solvent may be changed to a solvent of which hardly any decomposes at a high potential. In addition, in order to prevent reductive decomposition, an additive such as vinylene carbonate (VC) may be included. Furthermore, as a method of preventing decomposition of a nonaqueous electrolyte under a high-temperature environment, a method of forming a species on a surface of a positive electrode is known.

Solution to Problem

An electrode nonaqueous electrolyte battery according to an embodiment includes a current collector and a mixed layer formed on one surface or both surfaces of the current collector. The mixed layer includes an active material and a binding agent, and the ratio $I_2/I_1$ of the highest peak intensity $I_2$ in peaks appearing in the wavelength range of 1400 to 1480 $cm^{-1}$ to the highest peak intensity $I_1$ in peaks appearing in the wavelength range of 2200 to 2280 $cm^{-1}$ is 10 or more and 20 or less in an infrared absorption spectrum measured according to a total reflection measurement method. Alternatively, in the mixed layer, the ratio $I_3/I_2$ of the highest peak intensity $I_3$ in peaks appearing in the wavelength range of 1650 to 1850 $cm^{-1}$ to the highest peak intensity $I_2$ in peaks appearing in the wavelength range of 1400 to 1480 $cm^{-1}$ is 0.1 or more and 0.8 or less in the infrared absorption spectrum measured according to a total reflection measurement method.

DETAILED DESCRIPTION

A nonaqueous electrolyte battery electrode, a nonaqueous electrolyte battery, and a battery pack according to an embodiment will be described below with reference to the drawings. In the following description of the drawings, the same or similar parts are denoted with the same or similar reference numerals and redundant descriptions will be omitted. However, it should be noted that the drawings are schematic, and the relationship between the thickness and the planar size, the ratio between the thicknesses of layers, and the like may be different from those of actual components. Therefore, specific thicknesses and sizes should be determined with reference to the following description. Of course, parts having different size relationships and ratios are included in the drawings.

In addition, the following embodiments exemplify a device and a method for embodying the technical ideas of the invention. The technical ideas of the invention do not specify the materials, forms, structures, the arrangement, and the like of components as in the following. The technical ideas of the invention can be variously modified within the scope of the claims.

[First Embodiment]

A nonaqueous electrolyte battery electrode according to a first embodiment is provided. The nonaqueous electrolyte battery electrode of the present embodiment includes a current collector, and a mixed layer formed on one surface or both surfaces of the current collector. The mixed layer includes an active material and a binding agent (a binder). In addition, the nonaqueous electrolyte battery electrode is formed in a pellet form and can be used as an electrode of the nonaqueous electrolyte battery.

In an infrared absorption spectrum measured according to an attenuated total reflection (ATR, total reflection measurement) method, in the mixed layer of the nonaqueous electrolyte battery electrode according to the embodiment, the ratio $I_2/I_1$ of the highest peak intensity $I_2$ in peaks appearing in the wavelength range of 1400 to 1480 $cm^{-1}$ to the highest peak intensity $I_1$ in peaks appearing in the wavelength range of 2200 to 2280 $cm^{-1}$ is 10 or more and 20 or less. Alternatively, in an infrared absorption spectrum measured according to the ATR method, the ratio $I_3/I_2$ of the highest peak intensity $I_3$ in peaks appearing in the wavelength range of 1650 to 1850 $cm^{-1}$ to the highest peak intensity $I_2$ in peaks appearing in the wavelength range of 1400 to 1480 $cm^{-1}$ is 0.1 or more and 0.8 or less. Preferably $I_2/I_1$ is 10 or more and 20 or less, and $I_3/I_2$ is 0.1 or more and 0.8 or less.

The ATR method is a method in which an ATR crystal (high refractive index medium) is pressure-bonded to a surface of a measurement target specimen, the totally reflected light that has entered the inside the specimen and then been reflected is measured, and thus an infrared absorption spectrum of a surface layer portion of the specimen is measured. Based on the infrared absorption spectrum measured using the ATR method, it is possible to analyze components of a species on the surface layer portion of the specimen. The infrared absorption spectrum can be measured using a Fourier transform infrared spectrophotometer (FT-IR).

The highest peak in peaks appearing in the wavelength range of 2200 to 2280 $cm^{-1}$ is a peak derived from a nitrile bond. The highest peak in peaks appearing in the wavelength range of 1400 to 1480 $cm^{-1}$ is considered to be a peak derived from lithium carbonate. When a nonaqueous electrolyte battery electrode including a mixed layer whose peak intensity ratio $I_2/I_1$ is in the range of 10 or more and 20 or less is used, it is possible to obtain a nonaqueous electrolyte battery having excellent life characteristics under a high-temperature environment. It is inferred that, when a binding agent or a species including a nitrile bond is present on a surface of the mixed layer of the nonaqueous electrolyte battery electrode and the species additionally includes a large amount of an inorganic carbonate material such as lithium carbonate, excessive decomposition of the nonaqueous electrolyte under a high-temperature environment and formation of an organic species accordingly are prevented. The peak intensity ratio $I_2/I_1$ is preferably 13 or more and 19 or less, and more preferably 14 or more and 18 or less.

The highest peak in peaks appearing in the wavelength range of 1650 to 1850 $cm^{-1}$ is considered to be a peak derived from the organic species. When a nonaqueous electrolyte battery electrode including a mixed layer having a surface on which a species containing a smaller amount of organic material than inorganic material such as lithium carbonate is formed is used, a nonaqueous electrolyte battery having excellent life characteristics under a high-temperature environment is obtained. This is considered to be because when the amount of organic species is smaller than the amount of the inorganic species formed on the surface of the mixed layer of the nonaqueous electrolyte battery electrode, the electrical resistance of the mixed layer decreases. When the ratio $I_3/I_2$ of the peak intensity $I_3$ in the peak derived from the organic species to the peak intensity $I_2$ in the peak derived from the carbonate is 0.1 or more and 0.8 or less, the above effect is enhanced. The peak intensity ratio $I_3/I_2$ is preferably 0.15 or more and 0.6 or less, and more preferably 0.2 or more and 0.4 or less.

It is more desirable that the peak intensity ratios for both of the above $I_2/I_1$ and $I_3/I_2$ be satisfied.

As an active material included in the mixed layer of the nonaqueous electrolyte battery electrode, for example, a manganese dioxide ($MnO_2$), iron oxide, copper oxide, and nickel oxide, a lithium manganese composite oxide (for example, $Li_xMn_2O_4$ or $Li_xMnO_2$), a lithium nickel composite oxide (for example, $Li_xNiO_2$), a lithium cobalt composite oxide (for example, $Li_xCoO_2$), a lithium nickel cobalt composite oxide (for example, $Li_xNi_{1-y}Co_yO_2$), a lithium manganese cobalt composite oxide (for example, $Li_xMn_yCo_{1-y}O_2$), a lithium nickel cobalt manganese composite oxide (for example, $LiNi_{1-y-z}Co_yMn_zO_2$), a lithium nickel cobalt aluminum composite oxide (for example, $Li_xNi_{1-y-z}Co_yAl_zO_2$), a lithium manganese nickel composite oxide having a spinel structure (for example, $Li_xMn_{2-y}Ni_yO_4$), a lithium phosphorus oxide having an olivine structure (for example, $Li_xFePO_4$, $Li_xMnPO_4$, $LiMn_{1-y}Fe_yPO_4$, and $Li_xCoPO_4$), iron sulfate ($Fe_2(SO_4)_3$) and a vanadium oxide (for example, $V_2O_5$) may be exemplified. In the above chemical formulas, x, y, and z satisfy $0<x\leq1$, $0<y<1$, and $0<z<1$. In the electrode-active material, these compounds may be used alone, or a plurality of compounds may be used in combination.

As a more preferable electrode-active material, for example, a lithium manganese composite oxide ($Li_xMn_2O_4$), a lithium cobalt composite oxide ($Li_xCoO_2$), a lithium nickel cobalt composite oxide ($Li_xNi_{1-y}Co_yO_2$), a lithium manganese cobalt composite oxide ($Li_xMn_yCo_{1-y}O_2$), a lithium nickel cobalt manganese composite oxide ($Li_xNi_{1-y-z}Co_yMn_zO_2$), and a lithium phosphorus oxide having an olivine structure (for example, $Li_xFePO_4$, $Li_xMnPO_4$, $Li_xMn_{1-y}Fe_yPO_4$, and $Li_xCoPO_4$) may be exemplified. In the above chemical formulas, x, y, and z satisfy $0<x\leq1$, $0<y<1$, and $0<z<1$.

As a particularly preferable electrode-active material, a lithium nickel cobalt manganese composite oxide ($Li_xNi_{1-y-z}Co_yMn_zO_2$), a lithium manganese composite oxide ($Li_xMn_2O_4$), a lithium cobalt composite oxide ($Li_xCoO_2$), a lithium iron phosphate ($Li_xFePO_4$), and a lithium manganese iron phosphate ($Li_xMn_{1-y}Fe_yO_4$) may be exemplified. In the above chemical formulas, x, y, and z satisfy $0<x\leq1$, $0<y<1$, and $0<z<1$. The lithium manganese composite oxide ($Li_xMn_2O_4$) includes a lithium aluminum manganese composite oxide ($Li_xMn_{2-a}Al_aO_4$, $0<a\leq1$) in which some Mn is substituted with Al. The lithium manganese iron phosphate ($Li_xMn_{1-y}Fe_yPO_4$) includes a manganese iron magnesium lithium phosphate ($Li_xMn_{1-b-c}Fe_bMg_cPO_4$, $0<b+c<1$) in which some Mn is substituted with Mg.

In the nonaqueous electrolyte battery electrode according to the first embodiment, the mixed layer may include a conductive agent. Examples of the conductive agent include a carbonaceous material such as acetylene black, carbon black, graphite (graphite), carbon nanofibers and carbon nanotubes. These carbonaceous materials may be used alone or a plurality of carbonaceous materials may be used.

The binding agent that is additionally included in the mixed layer of the nonaqueous electrolyte battery electrode according to the first embodiment binds an electrode-active material, a conductive agent and a current collector. As the binding agent, an organic material having a nitrile bond is preferably used. As the organic material having a nitrile bond, polyacrylonitrile, may be exemplified. In addition, the binding agent may be polytetrafluoroethylene (PTFE), polyvinylidene fluoride (PVdF), fluorine-based rubber, and an acrylic resin of polyacrylic acid or a copolymer thereof.

The proportions of the electrode-active material, the conductive agent, and the binding agent included in the mixed layer of the nonaqueous electrolyte battery electrode are preferably in the range of 80 mass % or more and 96 mass % or less for the electrode-active material, in the range of 3 mass % or more and 18 mass % or less for the conductive material, and in the range of 1 mass % or more and 17 mass % or less for the binding agent. When the proportion of the conductive agent is set to 3 mass % or more, current collection performance of the mixed layer is improved, and the mixed layer can exhibit excellent charging and discharging characteristics. When the ratio of the conductive agent is set to 18 mass % or less, it is possible to reduce decomposition of the nonaqueous electrolyte on the surface of the conductive agent during high-temperature storage. When the ratio of the binding agent is set to 1 mass % or more, a sufficient electrode strength is obtained. When the proportion of the binding agent is set to 17 mass % or less, it is possible to reduce an amount of the binding agent that is an insulating material mixed into the electrode and decrease the internal resistance.

According to the nonaqueous electrolyte battery electrode of the first embodiment described above, in an infrared absorption spectrum measured according to the ATR method, the ratio $I_2/I_1$ of the highest peak intensity $I_2$ in peaks appearing in the wavelength range of 1400 to 1480 $cm^{-1}$ to the highest peak intensity $I_1$ in peaks appearing in the wavelength range of 2200 to 2280 $cm^{-1}$ is 10 or more and 20 or less, and a species including a large amount of an inorganic material which hardly decomposes a nonaqueous electrolyte under a high-temperature environment is formed. Therefore, the nonaqueous electrolyte battery using the nonaqueous electrolyte battery electrode of the present embodiment has improved life characteristics under a high-temperature environment.

In addition, according to the nonaqueous electrolyte battery electrode of the present embodiment, in an infrared absorption spectrum measured according to the ATR method, the ratio $I_3/I_2$ of the highest peak intensity $I_3$ in peaks appearing in the wavelength range of 1650 to 1850 $cm^{-1}$ to the highest peak intensity $I_2$ in peaks appearing in the wavelength range of 1400 to 1480 $cm^{-1}$ is 0.1 or more and 0.8 or less, and the electrical resistance is low under a high-temperature environment. Therefore, the nonaqueous electrolyte battery using the nonaqueous electrolyte battery electrode of the present embodiment has improved life characteristics under a high-temperature environment.

[Second Embodiment]

According to a second embodiment, a nonaqueous electrolyte battery is provided.

Figure 1:
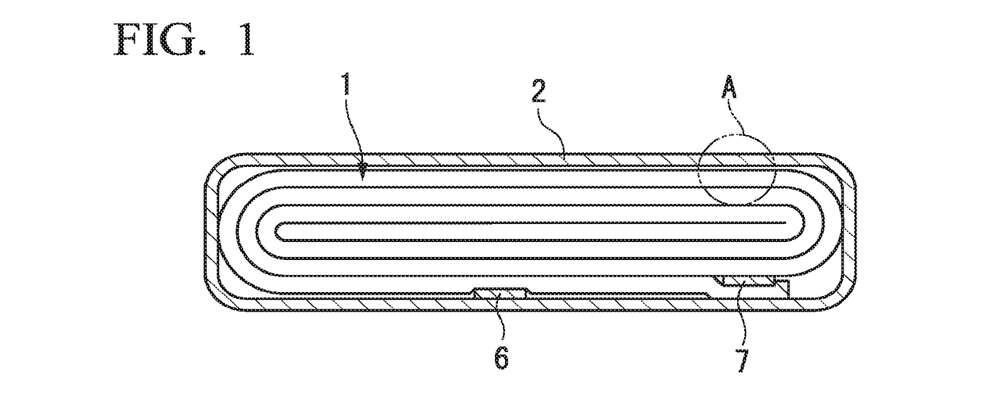
FIG. 1 is a cross-sectional view of an example of a nonaqueous electrolyte battery according to a second embodiment.
Figure 2:
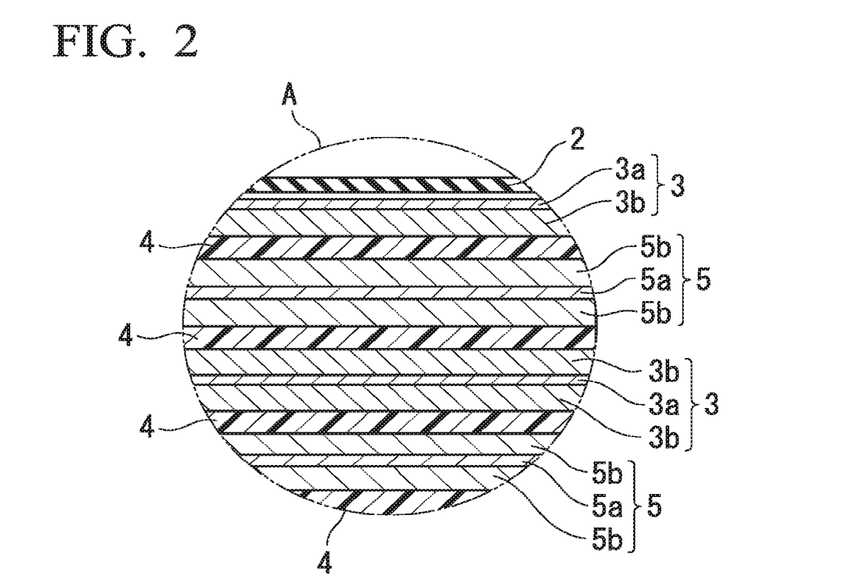
FIG. 2 is an enlarged cross-sectional view of a part A in FIG. 1.

The nonaqueous electrolyte battery according to the second embodiment will be described in detail with reference to FIG. 1 and FIG. 2. FIG. 1 is a cross-sectional view of an example of the nonaqueous electrolyte battery according to the second embodiment. FIG. 2 is an enlarged cross-sectional view of a part A in FIG. 1.

In the nonaqueous electrolyte battery shown in FIG. 1 and FIG. 2, a winding electrode group 1 is stored in a bag-like exterior member 2 formed of a laminate film with a metal layer interposed between two resin films. The winding electrode group 1 is formed by winding a laminate in which a negative electrode 3, a separator 4, a positive electrode 5, and a separator 4 are laminated in this order from the outside in a spiral shape and press molding the wound laminate. As shown in FIG. 2, the negative electrode 3 of the outermost layer has a configuration in which a negative electrode mixture layer 3b including a negative electrode-active material is formed on one inner side surface of a negative electrode current collector 3a. The remaining negative electrode 3 has a configuration in which the negative electrode mixture layer 3b is formed on both surfaces of the negative electrode current collector 3a. The positive electrode 5 has a configuration in which a positive electrode mixture layer 5b is formed on both surfaces of a positive electrode current collector 5a.

In the vicinity of the outer peripheral end of the winding electrode group 1, a negative electrode terminal 6 is connected to the negative electrode current collector 3a of the negative electrode 3 of the outermost layer, and a positive electrode terminal 7 is connected to the positive electrode current collector 5a of the inside positive electrode 5. The negative electrode terminal 6 and the positive electrode terminal 7 extend from an opening of the bag-like exterior member 2 to the outside. For example, a liquid nonaqueous electrolyte is injected from the opening of the bag-like exterior member 2. When the opening of the bag-like exterior member 2 is thermally sealed with the negative electrode terminal 6 and the positive electrode terminal 7 therebetween, the winding electrode group 1 and the liquid nonaqueous electrolyte are completely sealed.

Figure 3:
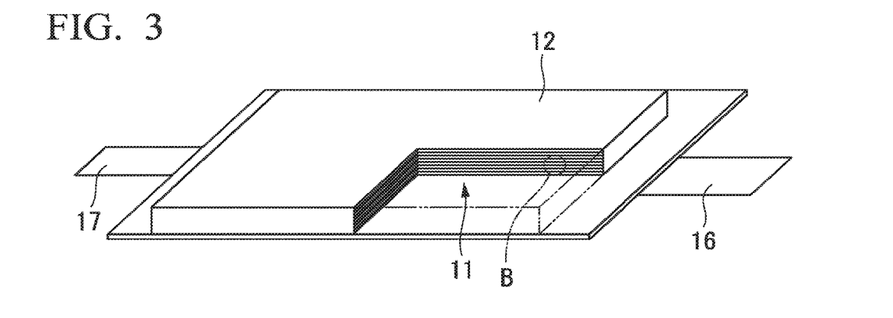
FIG. 3 is a partially cutaway perspective view of another example of the nonaqueous electrolyte battery according to the second embodiment.
Figure 4:
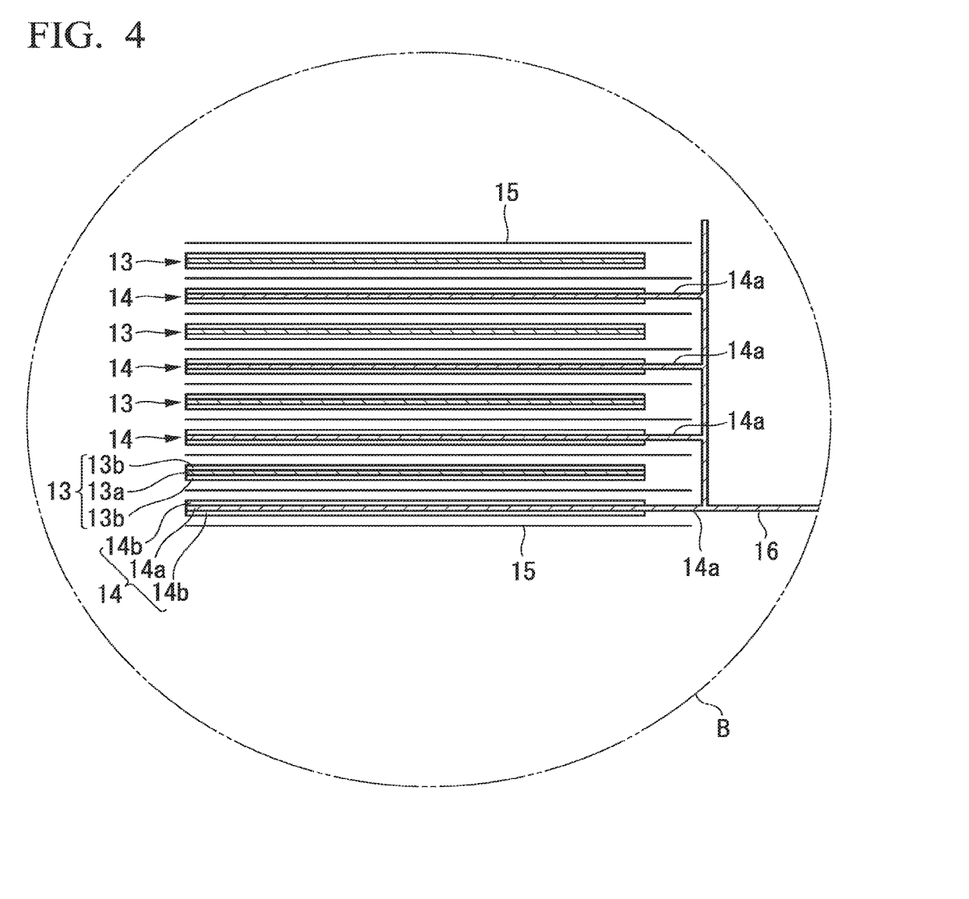
FIG. 4 is an enlarged cross-sectional view of a part B in FIG. 3.

The configuration of the nonaqueous electrolyte battery according to the second embodiment is not limited to the configuration shown in FIG. 1 and FIG. 2 described above, and may be, for example, a configuration shown in FIG. 3 and FIG. 4. FIG. 3 is a partially cutaway perspective view of another example of the nonaqueous electrolyte battery according to the second embodiment. FIG. 4 is an enlarged cross-sectional view of a part B in FIG. 3.

In the nonaqueous electrolyte battery shown in FIG. 3 and FIG. 4, a laminated electrode group 11 is stored in an exterior member 12 formed of a laminate film with a metal layer interposed between two resin films. As shown in FIG. 4, the laminated electrode group 11 has a structure in which positive electrodes 13 and negative electrodes 14 are alternately laminated with separators 15 therebetween.

A plurality of positive electrodes 13 are provided with each including a positive electrode current collector 13a and a positive electrode mixture layer 13b supported on both surfaces of the positive electrode current collector 13a. A plurality of negative electrodes 14 are provided with each including a negative electrode current collector 14a and a negative electrode mixture layer 14b supported on both surfaces of the negative electrode current collector 14a. One side of the negative electrode current collector 14a of each of the negative electrodes 14 protrudes from the positive electrode 13. The protruding negative electrode current collector 14a is electrically connected to a band-like negative electrode terminal 16. The tip of the band-like negative electrode terminal 16 is drawn out from the exterior member 12 to the outside. In addition, although not shown, in the positive electrode current collector 13a of the positive electrode 13, the side opposite to the side from which the negative electrode current collector 14a protrudes from the negative electrode 14. The positive electrode current collector 13a protruding from the negative electrode 14 is electrically connected to a band-like positive electrode terminal 17. The tip of the band-like positive electrode terminal 17 is positioned on the side opposite to the negative electrode terminal 16, and is drawn out from the side of the exterior member 12 to the outside.

The positive electrode, the negative electrode, the nonaqueous electrolyte, the separator, the exterior member, the positive electrode terminal, and the negative electrode terminal used in the nonaqueous electrolyte battery of the present embodiment will be described below in detail.

(Positive Electrode)

The positive electrode includes a positive electrode current collector and a positive electrode mixture layer. The positive electrode mixture layer is formed on one surface or both surfaces of the positive electrode current collector. In the positive electrode mixture layer, in infrared absorption spectrums measured according to the ATR method, the ratio $I_2/I_1$ of the highest peak intensity $I_2$ in peaks appearing in the wavelength range of 1400 to 1480 $cm^{-1}$ to the highest peak intensity $I_1$ in peaks appearing in the wavelength range of 2200 to 2280 $cm^{-1}$ is 10 or more and 20 or less. Alternatively, in the positive electrode mixture layer, in infrared absorption spectrums measured according to the ATR method, the ratio $I_3/I_2$ of the highest peak intensity $I_3$ in peaks appearing in the wavelength range of 1650 to 1850 $cm^{-1}$ to the highest peak intensity $I_2$ in peaks appearing in the wavelength range of 1400 to 1480 $cm^{-1}$ is 0.1 or more and 0.8 or less. In the positive electrode mixture layer, preferably, $I_2/I_1$ is 10 or more and 20 or less, and $I_3/I_2$ is 0.1 or more and 0.8 or less.

As a method of setting $I_2/I_1$ and $I_3/I_2$ of the positive electrode mixture layer measured according to the ATR method to be in the above ranges, a method in which a nonaqueous electrolyte battery is stored (aged) for a certain time under a high-temperature environment may be exemplified. Specifically, a method in which, at any state of charge (SOC) of 0 to 100% SOC, a nonaqueous electrolyte battery is aged for 3 hours or more under a high-temperature environment at 80° C. or more and 95° C. or less may be exemplified. In this case, when a gas is generated in the battery, the gas may be removed. When no gas is generated, gas removal need not be performed. If an organic material having a nitrile bond is used as the binding agent of the positive electrode mixture layer and a nonaqueous electrolyte in which an additive that easily forms a carbonate is added is used, when aging is performed under a high-temperature environment, an inorganic species is formed so that $I_2/I_1$ is in the above range, and formation of an excess organic species can be prevented, and $I_3/I_2$ is in the above range.

Next, a method of measuring infrared absorption spectrums of the positive electrode mixture layer according to the ATR method will be described. In order to measure infrared absorption spectrums of the positive electrode mixture layer according to the ATR method, it is necessary to disassemble the nonaqueous electrolyte battery and extract the positive electrode. The disassembling operation of the nonaqueous electrolyte battery is performed after the battery is brought into a discharge state. The discharge state of the battery is a state in which a constant current discharge is performed to 1.5 V at a current of 0.2 C in an environment at 25° C. In order to set nonaqueous electrolyte batteries connected in series to be in a discharge state, the number of batteries in series×1.5 is set as a discharge cutoff voltage. For example, when five nonaqueous electrolyte batteries are connected in series, a discharge cutoff voltage is 5×1.5=7.5 V.

The positive electrode extracted from the nonaqueous electrolyte battery is immersed in an ethyl methyl carbonate solvent, washed and then dried. The disassembling of the battery, and the extraction, and washing and drying of the positive electrode are performed under an inert atmosphere such as an argon atmosphere.

The dried positive electrode is cut into 3 mm squares in a glove box under a nitrogen atmosphere and is set in an ATR holder having an ATR crystal, and the positive electrode mixture layer of the positive electrode and the ATR crystal are pressure-bonded. In this case, a dew point in the glove box is −50° C. The ATR holder is extracted from the glove box and is attached to an FT-IR spectrometer. Since the positive electrode mixture layer is pressure-bonded to the AIR crystal, the AIR holder can be attached to the FT-IR spectrometer without bringing the positive electrode mixture layer into contact with air. For measurement of infrared absorption spectrums, the FT-IR spectrometer is purged with nitrogen gas, an ATR mode is set, and the total number of scans is 256. As the ATR crystal, a Ge crystal is used, and the angle of incidence of infrared light is 45°. The obtained infrared absorption spectrum needs to be corrected in order to remove the background. A base line is corrected so that both ends of a peak in the infrared absorption spectrum become flat.

The positive electrode mixture layer includes a positive electrode-active material, a conductive agent, and a binding agent. As the positive electrode-active material, the binding agent, and the conductive agent, the compounds exemplified in the first embodiment can be used.

The positive electrode current collector is preferably an aluminum foil or an aluminum alloy foil containing at least one element selected from the group consisting of Mg, Ti, Zn, Mn, Fe, Cu, and Si. The thickness of the aluminum foil or the aluminum alloy foil is preferably 20 μm or less and more preferably 15 μm or less. The purity of the aluminum foil is preferably 99% or more. When a transition metal such as Fe, Cu, Ni, and Cr is included, the content thereof is preferably 1 mass % or less.

The density of the positive electrode mixture layer is preferably 3 g/cm$^3$ or more.

The positive electrode can be produced, for example, according to the following method. First, a positive electrode-active material, a conductive agent, and a binding agent are suspended in a solvent to prepare a slurry. The slurry is applied to one surface or both surfaces of a current collector, and dried to form a positive electrode mixture layer. Then, pressing is performed. Alternatively, a positive electrode-active material, a conductive agent, and a binding agent can be formed in a pellet form and used as a positive electrode mixture layer.

(Negative Electrode)

The negative electrode includes a negative electrode current collector and a negative electrode mixture layer. The negative electrode mixture layer is formed on one surface or both surfaces of the negative electrode current collector.

The negative electrode mixture layer includes a negative electrode-active material, a conductive agent, and a binding agent.

Examples of the negative electrode-active material include a carbonaceous material such as graphite and hard carbon, a spinel type lithium titanate, an orthorhombic Na-containing niobium titanium complex oxide, $Ti_{1-x}M1_xNb_{2-y}M2_yO_{7-\delta}$ (0≤x<1, 0≤y<1, −0.5≤δ≤0.5, M1 and M2 denote at least one metal element selected from the group consisting of Mg, Fe, Ni, Co, W, Ta, and Mo, and the M1 and the M2 may be the same metal element or metal elements that are different from each other), a monoclinic titanium composite oxide, an anatase type titanium composite oxide, and a titanium-containing oxide such as Ramsdellite type lithium titanate, $TiNb_2O_7$, and $Ti_2Nb_2O_9$. The orthorhombic Na-containing niobium titanium complex oxide indicates $Li_{2+v}Na_{2-w}M1_xTi_{6-y-z}Nb_yM2_zO_{14+\delta}$ (M1 denotes at least one metal element selected from the group consisting of Cs, K, Sr, Ba, and Ca, and M2 denotes at least one metal element selected from the group consisting of Zr, Sn, V, Ta, Mo, W, Fe, Co, Mn, and Al, 0≤v≤4, 0<w<2, 0≤x<2, 0<y≤6, 0≤z<3, −0.5≤δ≤0.5).

The negative electrode-active material is preferably a carbonaceous material, a lithium titanate having a spinel structure, an orthorhombic Na-containing niobium titanium complex oxide, $Ti_{1-x}M1_xNb_{2-y}M2_yO_{7-\delta}$, a monoclinic titanium composite oxide, and a titanium-containing oxide such as $TiNb_2O_7$ and $Ti_2Nb_2O_9$. Graphite, hard carbon, a spinel type lithium titanate, an orthorhombic Na-containing niobium titanium complex oxide, $Ti_{1-x}M1_xNb_{2-y}M2_yO_{7-\delta}$ and a monoclinic titanium composite oxide are particularly preferable.

The conductive agent improves current collection performance and minimizes a contact resistance between the active material and the current collector. Examples of the conductive agent include carbonaceous materials such as acetylene black, carbon black, graphite, carbon nanofibers and carbon nanotubes. These carbonaceous materials may be used alone or a plurality of carbonaceous materials may be used.

The binding agent binds the active material, the conductive agent, and the current collector. The binding agent may be polytetrafluoroethylene (PTFE), polyvinylidene fluoride (PVdF), styrene butadiene rubber (SBR), carboxymethyl cellulose (CMC), fluorine-based rubber, and an acrylic resin of polyacrylic acid or a copolymer thereof.

The combinational proportions of the negative electrode-active material, the conductive agent, and the binding agent are preferably in the range of 70 mass % or more and 97 mass % or less for the negative electrode-active material, in the range of 2 mass % or more and 28 mass % or less for the negative electrode conductive agent, and in the range of 1 mass % or more and 28 mass % or less for the binding agent. When the mixing ratio of the conductive agent is less than 2 mass %, there is a risk of current collection performance of the negative electrode mixture layer decreasing and high current characteristics of the nonaqueous electrolyte battery deteriorating. In addition, when the mixing ratio of the binding agent is less than 1 mass %, there is a risk of the binding property between the negative electrode mixture layer and the negative electrode current collector deteriorating and cycle characteristics deteriorating. Meanwhile, in consideration of high capacity, the mixing ratio of the conductive agent and the mixing ratio of the binding agent are preferably 28 mass % or less.

The negative electrode current collector is preferably formed of a copper foil, a stainless steel foil, a nickel foil, an aluminum foil or an aluminum alloy foil containing an element such as Mg, Ti, Zn, Mn, Fe, Cu and Si which is electrochemically stable in the potential range of 0.0 V to 3.0 V.

The negative electrode can be produced, for example, according to the following method. First, a negative electrode-active material, a conductive agent, and a binding agent are suspended in a solvent to prepare a slurry. The slurry is applied to one surface or both surfaces of the negative electrode current collector and dried to form a negative electrode mixture layer. Then, pressing is performed. Alternatively, a negative electrode-active material, a conductive agent, and a binding agent can be formed in a pellet form and used as a negative electrode mixture layer.

(Nonaqueous Electrolyte)

Examples of the nonaqueous electrolyte include a liquid nonaqueous electrolyte prepared by dissolving an electrolyte in an organic solvent, a gel-like organic electrolyte in which a liquid organic solvent and a polymer material are combined, and a solid nonaqucous electrolyte in which a lithium salt electrolyte and a polymer material are combined. In addition, a room-temperature molten salt (ionic melt) containing lithium ions may be used as the nonaqueous electrolyte. As the polymer material, for example, polyvinylidene fluoride (PVdF), polyacrylonitrile (PAN), and polyethylene oxide (PEO) may be exemplified. A liquid or gel-like nonaqueous electrolyte having a boiling point of 100° C. or more and containing an organic electrolyte or a room-temperature molten salt is preferable. The liquid organic electrolyte is prepared by dissolving an electrolyte with a concentration of 0.5 to 2.5 mol/L in an organic solvent. Accordingly, it is possible to obtain a high output under a low-temperature environment. In the organic electrolyte, the concentration of the electrolyte is more preferably in the range of 1.5 to 2.5 mol/L. Here, the liquid nonaqueous electrolyte may be referred to as a nonaqueous electrolyte solution.

Examples of the electrolyte include lithium salts such as lithium perchlorate ($LiClO_4$), lithium hexafluorophosphate ($LiPF_6$), lithium tetrafluoroborate ($LiBF_4$), lithium arsenic hexafluoride ($LiAsF_6$), lithium trifluoromethasulfonate ($LiCF_3SO_3$), lithium bis(trifluoromethanesulfonyl)imide [$LiN(CF_3SO_2)_2$] and lithium tristrifluoromethylsulfonate ($Li(CF_3SO_2)_3C$). These electrolytes can be used alone or in a combination of two or more thereof. Among them, an electrolyte including lithium hexafluorophosphate ($LiPF_6$) is preferable because it hardly oxidizes at a high potential.

Examples of the organic solvent include a cyclic carbonate such as propylene carbonate (PC), ethylene carbonate (EC), and vinylene carbonate (VC); a chain carbonate such as diethyl carbonate (DEC), dimethyl carbonate (DMC), and methyl ethyl carbonate (MEC); a cyclic ether such as tetrahydrofuran (THF) 2-methyltetrahydrofuran (2MeTHF), and dioxolane (DOX); a chain ether such as dimethoxyethane (DME), and diethoxyethane (DEE); acetonitrile (AN) and sulfolane (SL). These organic solvents can be used alone or in a combination of two or more thereof.

As a more preferable organic solvent, a solvent mixture that includes a first solvent including at least one selected from the group consisting of propylene carbonate (PC), ethylene carbonate (EC) and γ-butyrolactone (GBL) and a second solvent including at least one chain carbonate selected from the group consisting of diethyl carbonate (DEC), dimethyl carbonate (DMC) and methyl ethyl carbonate (MEC) may be exemplified. This solvent mixture has high stability at a high potential of 4.4 to 4.5 V. When such a solvent mixture is used, it is possible to obtain a nonaqueous electrolyte battery having excellent high-temperature characteristics and low-temperature characteristics. In the solvent mixture including the first solvent and the second solvent, the mixing ratio of the second solvent is preferably 70 volume % or more.

An additive can be added to the electrolyte solution. An additive that forms an inorganic compound such as $Li_2CO_3$ is preferable. As a compound that forms a species of an inorganic compound, for example, $LiPF_2O_2$, $Li_2PFO_3$, lithium bisoxalate borate (LiBOB), lithium oxalate difluoroborate (LiODFB), tris(trimethylsilyl)borate (TMSB), tris (trimethylsilyl)phosphate (TMSP), and fluoroethylene carbonate (FEC) may be exemplified. The concentration of such a compound is preferably in the range of 0.1 to 5 mass % with respect to the total amount of the nonaqueous electrolyte.

(Separator)

As the Separator, a Porous Film Formed of a Material, for Example, Polyethylene (PE), polypropylene (PP), polyethylene terephthalate (PET), cellulose or polyvinylidene fluoride (PVdF), a synthetic resin nonwoven fabric, or the like can be used. Further, a separator in which an inorganic compound is applied to a porous film can be used.

(Exterior Member)

As the exterior member, a bag-like container formed of a laminate film or a metal container may be used.

The shape thereof includes a flat shape, a square shape, a cylindrical shape, a coin shape, a button shape, a sheet shape, and a laminate shape. Here, of course, the exterior member may be used for a large battery mounted in a two-wheel to four-wheel vehicle and the like in addition to a small battery mounted in a portable electronic device or the like.

As the laminate film, a multilayer film in which a metal layer is interposed between resin films is used. The metal layer is preferably an aluminum foil or an aluminum alloy foil for weight reduction. For the resin film, a polymer material, for example, polypropylene (PP), polyethylene (PE), nylon, and polyethylene terephthalate (PET), can be used. The laminate film can be formed into the shape of the exterior member according to sealing through thermal fusion. The thickness of the laminate film is preferably 0.2 mm or less.

The metal container can be formed of aluminum or an aluminum alloy. The aluminum alloy preferably includes an element such as magnesium, zinc, or silicon. Here, the content of a transition metal such as iron, copper, nickel, or chromium is preferably 100 ppm or less. Therefore, it is possible to significantly improve long-term reliability and heat dissipation under a high-temperature environment. The thickness of the metal container is preferably 0.5 mm or less, and more preferably 0.2 mm or less.

(Positive Electrode Terminal)

The positive electrode terminal is formed of a material that is electrically stable in the range of 3.0 V or more and 4.5 V or less that is a potential with respect to metallic lithium ions and has conductivity. The positive electrode terminal is preferably formed of aluminum or an aluminum alloy containing an element such as Mg, Ti, Zn, Mn, Fe, Cu, and Si. The positive electrode terminal is preferably formed of the same material as that of the positive electrode current collector in order to reduce a contact resistance with respect to the positive electrode current collector.

(Negative Electrode Terminal)

The negative electrode terminal is formed of a material that is electrically stable in the range of 1.0 V or more and 3.0 V or less that is a potential with respect to metallic lithium ions and has conductivity. The negative electrode terminal is preferably formed of copper, stainless steel, nickel, aluminum, or an aluminum alloy containing an element such as Mg, Ti, Zn, Mn, Fe, Cu, and Si. The negative electrode terminal is preferably formed of the same material as that of the negative electrode current collector in order to reduce a contact resistance with respect to the negative electrode current collector.

According to the second embodiment described above, since the nonaqueous electrolyte battery electrode according to the first embodiment described above is used as the positive electrode, it is possible to provide a nonaqueous electrolyte battery having excellent life characteristics under a high-temperature environment.

[Third Embodiment]

According to a third embodiment, a pack battery is provided.

The battery pack according to the present embodiment includes two or more of the above nonaqueous electrolyte batteries according to the second embodiment (that is, a single cell). Two or more nonaqueous electrolyte batteries are arranged to be electrically connected in series or in parallel.

The battery pack will be described in detail with reference to FIG. 5 and FIG. 6. In the battery pack shown in FIG. 5, the nonaqueous electrolyte secondary battery shown in FIG. 1 is used as a single cell 21.

A plurality of single cells 21 are laminated so that the negative electrode terminal 6 and the positive electrode terminal 7 extending to the outside are aligned in the same direction, and are fastened using an adhesive tape 22 to form an assembled battery 23. As shown in FIG. 6, these single cells 21 are electrically connected to each other in series.

A printed wiring board 24 is arranged to face a side surface of the single cell 21 from which the negative electrode terminal 6 and the positive electrode terminal 7 extend. As shown in FIG. 6, a thermistor 25, a protective circuit 26, and an energizing terminal 27 for an external device are mounted on the printed wiring hoard 24. Here, on a surface of the printed wiring board 24 that faces the assembled battery 23, an insulating plate (not shown) is attached in order to avoid an unnecessary connection with a wiring of the assembled battery 23.

A positive electrode-side lead 28 is connected to the positive electrode terminal 7 positioned on the lowermost layer of the assembled battery 23, and a tip thereof is inserted into a positive electrode-side connector 29 of the printed wiring board 24 and electrically connected thereto. A negative electrode-side lead 30 is connected to the negative electrode terminal 6 positioned on the uppermost layer of the assembled battery 23, and a tip thereof is inserted into a negative electrode-side connector 31 of the printed wiring board 24 and electrically connected thereto. The connectors 29 and 31 are connected to the protective circuit 26 through wirings 32 and 33 formed on the printed wiring board 24.

The thermistor 25 detects the temperature of the single cell 21 and transmits a detection signal to the protective circuit 26. The protective circuit 26 can block a positive side wiring 34a and a negative side wiring 34b between the protective circuit 26 and the energizing terminal 27 for an external device under predetermined conditions. The predetermined conditions include that, for example, a temperature detected by the thermistor 25 is a predetermined temperature or higher. In addition the predetermined conditions include that an overcharge, an overdischarge, an overcurrent, or the like of the single cell 21 has been detected. The detection of such an overcharge is performed for each of the single cells 21 individually or all of the single cells 21. When detection is performed for each of the single cells 21, a battery voltage may be detected, or a positive electrode potential or a negative electrode potential may be detected. In the case of the latter, a lithium electrode used as a reference electrode is inserted into each of the single cells 21. In FIG. 5 and FIG. 6, a wiring 35 for voltage detection is connected to each of the single cells 21, and a detection signal is transmitted to the protective circuit 26 through the wiring 35.

Protective sheets 36 made of rubber or a resin are arranged on three side surfaces of the assembled battery 23. Specifically, the protective sheets 36 are arranged on three side surfaces except the side surface from which the positive electrode terminal 7 and the negative electrode terminal 6 protrude among side surfaces of the assembled battery 23.

The assembled battery 23 is stored in a storage container 37 together with the protective sheets 36 and the printed wiring board 24. That is, the protective sheets 36 are arranged on both inner sides of the storage container 37 in the long side direction and one inner side in the short side direction. The printed wiring board 24 is arranged on an inner side opposite to the protective sheet 36 arranged in the short side direction. The assembled battery 23 is positioned in a space surrounded by the protective sheet 36 and the printed wiring board 24. A cover 38 is attached to the upper surface of the storage container 37.

Here, in place of the adhesive tape 22, a heat-shrinkable tape may be used to fix the assembled battery 23. In this case, protective sheets are arranged on both side surfaces of the assembled battery, a heat-shrinkable tape is wound therearound, and the heat-shrinkable tape is then thermally shrunk to bind the assembled battery.

Figure 5:
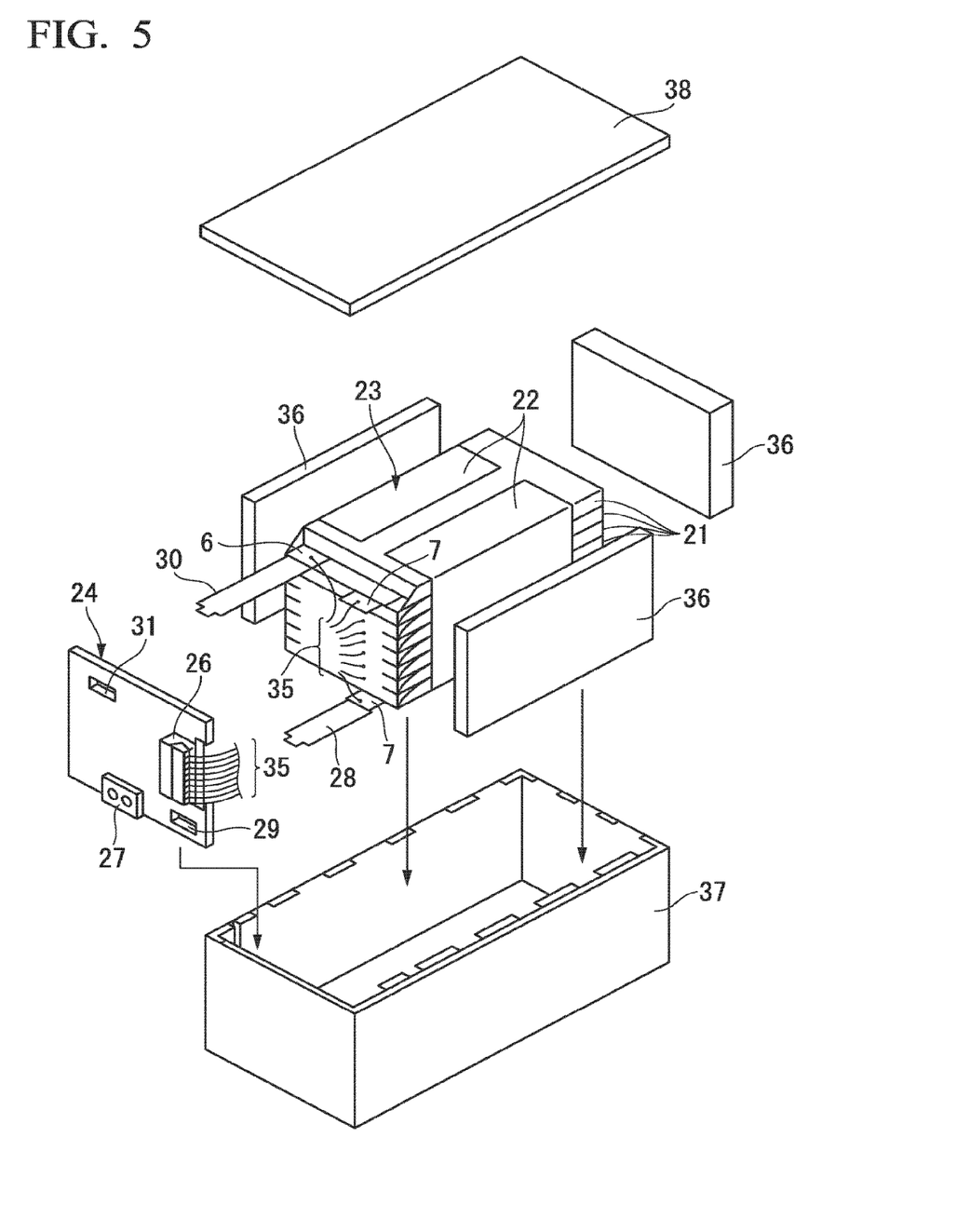
FIG. 5 is an exploded perspective view of a battery pack according to a third embodiment.
Figure 6:
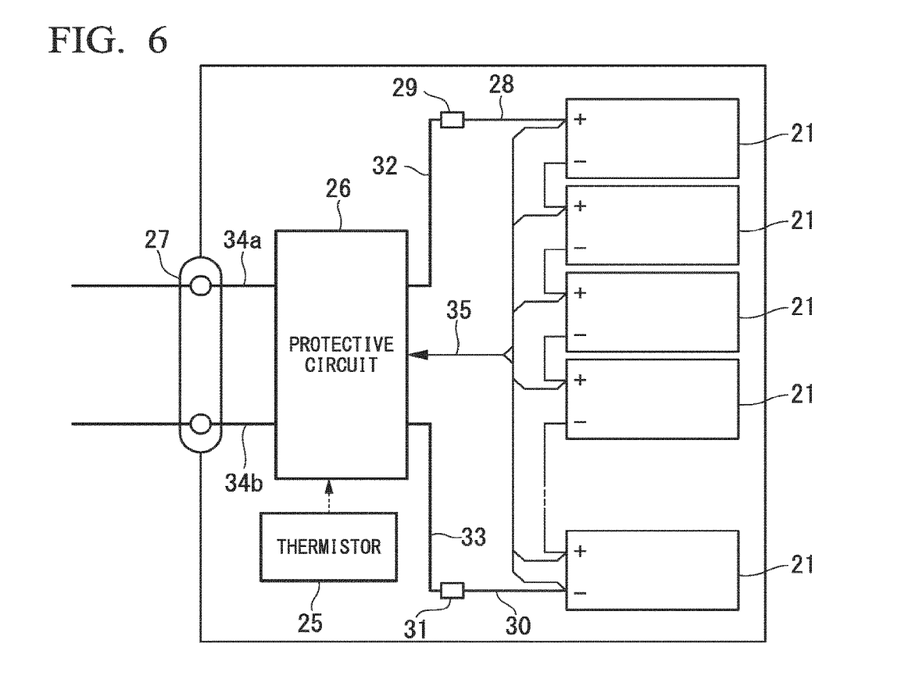
FIG. 6 is a block diagram showing an electric circuit of the battery pack in FIG. 5.

While the single cells 21 are connected in series in FIG. 5 and FIG. 6, they may be connected in parallel in order to increase a battery capacity. The assembled battery packs may be connected in series or in parallel.

Here, the mode of the battery pack may be appropriately changed depending on applications. For applications of the battery pack of the embodiment, preferably, exhibiting of excellent cycle performance when a high current is output is required. Specifically, a power supply of a digital camera, and automotive applications for two-wheel to four-wheel hybrid electric vehicles, two-wheel to four-wheel electric vehicles, and assisted bicycles may be exemplified. In particular, a battery pack using a nonaqueous electrolyte secondary battery having excellent high-temperature durability is suitably used for automotive applications.

According to the third embodiment described above, it is possible to provide a battery pack having excellent life characteristics under a high-temperature environment by using the nonaqueous electrolyte battery having excellent life characteristics according to the above second embodiment.

While several embodiments of the present invention have been described, these embodiments are only examples and are not intended to limit the scope of the invention. These embodiments can be implemented in various other forms, and various omissions, substitutions, and changes can be made without departing from the spirit and scope of the invention. These embodiments and modifications thereof are included in the spirit and scope of the invention, and fall within the inventions described in the appended claims and equivalents thereof.

EXAMPLES

Examples are described below, but the present invention is not limited to the following examples unless they exceed the scope of the present invention.

Example 1

(Production Of Positive Electrode)

90 mass % of $LiNi_{0.34}Co_{0.33}Mn_{0.33}O_2$ powder as a positive electrode-active material, 5 mass % of acetylene black as a conductive agent, and 5 mass % of polyacrylonitrile as a binding agent were added to N-methyl pyrrolidone (NMP) and mixed in to prepare a slurry. The slurry was applied to both surfaces of a current collector formed of an aluminum foil with a thickness of 15 μm, dried, and pressed to produce a positive electrode including a positive electrode mixture layer with a density of 3.2 $g/cm^3$.

(Production Of Negative Electrode)

90 mass % of $Li_4Ti_5O_{12}$ powder as a negative electrode-active material, 5 mass % of acetylene black as a conductive agent, and 5 mass % of polyvinylidene fluoride (PVdF) as a binding agent were added to N-methyl pyrrolidone (NMP) and mixed in to prepare a slurry. The slurry was applied to both surfaces of a current collector formed of an aluminum foil with a thickness of 15 μm and dried. The current collector and the dried slurry were pressed to produce a negative electrode including a negative electrode mixture layer with a density of 2.0 $g/cm^3$.

(Production of Electrode Group)

The positive electrode, a separator formed of a polyethylene porous film with a thickness of 25 μm, the negative electrode, and a separator were stacked in this order. Then, the obtained stack was wound in a spiral shape and thermally pressed at 90° C. to produce a flat electrode group with a width of 30 mm and a thickness of 3.0 mm. The obtained electrode group was accommodated in a pack formed of a laminate film and dried at 80° C. for 24 hours in a vacuum. The laminate film obtained by forming a polypropylene layer on both surfaces of an aluminum foil with a thickness of 40 μm and having a total thickness of 0.1 mm was used.

(Preparation of Liquid Nonaqueous Electrolyte)

Propylene carbonate (PC) and diethyl carbonate (DEC) were mixed at a volume ratio of 1:2 to prepare a solvent mixture. 1 M of $LiPF_6$ as an electrolyte was dissolved in the solvent mixture, and $LiPF_2O_2$ was additionally added at 1.5 mass % with respect to the total amount of a liquid nonaqueous electrolyte to prepare the liquid nonaqueous electrolyte.

(Production of Nonaqueous Electrolyte Battery)

The liquid nonaqueous electrolyte was injected into the laminate film pack in which the electrode group was accommodated. Then, the pack was completely sealed through thermal sealing to produce a nonaqueous electrolyte battery having the above structure shown in FIG. 1 and with a width of 35 mm, a thickness of 3.2 mm, and a height of 65 mm. The produced nonaqueous electrolyte battery was subjected to the following charging and discharging treatment and aging treatment.

(Charging and Discharging Treatment)

Charging and discharging of the nonaqueous electrolyte battery were performed three times in an environment at 25° C., a charging voltage of 2.6 V, a discharging voltage of 1.8 V, and a current rate of 0.2 C.

(Aging Treatment)

A nonaqueous electrolyte battery of which the state of charge had been adjusted to 50% SOC was then stored in an environment at 80° C. for 3 hours.

(Charging and Discharging Cycle Test)

Using the nonaqueous electrolyte battery after the aging treatment, a charging and discharging cycle test in an environment at 60° C. was performed. Charging was performed in a constant current and constant voltage mode. As charging conditions in the cycles, a charge rate was 10 C, and a charging voltage was 2.6 V. In addition, charge cutoff conditions were set as a time after 3 hours or a time at which a current value reached 0.05 C. Discharging was performed in a constant current mode. A discharge cutoff voltage was 1.8 V. The number of cycles that were performed in the charging and discharging cycle test was 1000.

Example 2

A nonaqueous electrolyte battery was produced in the same manner as in Example 1 except that, when a positive electrode was produced, as a positive electrode-active material, $LiNi_{0.5}Co_{0.2}Mn_{0.3}O_2$ powder was used in place of $LiNi_{0.34}Co_{0.33}Mn_{0.33}O_2$ powder, and a charging and discharging cycle test was performed.

Example 3

A nonaqueous electrolyte battery was produced in the same manner as in Example 1 except that, when a positive electrode was produced, as a positive electrode-active material, $LiNi_{0.6}Co_{0.2}Mn_{0.2}O_2$ powder was used in place of $LiNi_{0.34}Co_{0.33}Mn_{0.33}O_2$ powder, and a charging and discharging cycle test was performed.

Example 4

A nonaqueous electrolyte battery was produced in the same manner as in Example 1 except that, when a positive electrode was produced, as a positive electrode-active material, $LiNi_{0.8}Co_{0.1}Mn_{0.1}O_2$ powder was used in place of $LiNi_{0.34}Co_{0.33}Mn_{0.33}O_2$ powder, and a charging and discharging cycle test was performed.

Example 5

A nonaqueous electrolyte battery was produced in the same manner as in Example 1 except that, when a positive electrode was produced, as a positive electrode-active material, $LiAl_{0.15}Mn_{1.85}O_4$ powder was used in place of $LiNi_{0.34}Co_{0.33}Mn_{0.33}O_2$ powder, and when a charging and discharging treatment and a charging and discharging cycle test were performed, a charging voltage was set to 2.7 V, and a discharging voltage was set to 1.8 V, and a charging and discharging cycle test was performed.

Example 6

A nonaqueous electrolyte battery was produced in the same manner as in Example 1 except that, when a positive electrode was produced, as a positive electrode-active material, $LiFePO_4$ powder was used in place of $LiNi_{0.34}Co_{0.33}Mn_{0.33}O_2$ powder, and when a charging and discharging treatment and a charging and discharging cycle test were performed, a charging voltage was set to 2.1 V, and a discharging voltage was set to 1.6 V, and a charging and discharging cycle test was performed.

Example 7

A nonaqueous electrolyte battery was produced in the same manner as in Example 1 except that, when a positive electrode was produced, as a positive electrode-active material, $LiMn_{0.85}Fe_{0.1}Mg_{0.05}PO_4$ powder was used in place of $LiNi_{0.34}Co_{0.33}Mn_{0.33}O_2$ powder, and a charging and discharging cycle test was performed.

Example 8

A nonaqueous electrolyte battery was produced in the same manner as in Example 1 except that, when a positive electrode was produced, the amount of $LiNi_{0.34}Co_{0.33}Mn_{0.33}O_2$ powder was set to 72 mass %, and 18 mass % of $LiCoO_2$ powder was additionally added as a positive electrode-active material, and a charging and discharging cycle test was performed.

Example 9

A nonaqueous electrolyte battery was produced in the same manner as in Example 1 except that, when a positive electrode was produced, the amount of $LiNi_{0.34}Co_{0.33}Mn_{0.33}O_2$ powder was set to 45 mass %, and 45 mass % of $LiCoO_2$ powder was additionally added as a positive electrode-active material, and a charging and discharging cycle test was performed.

Example 10

A nonaqueous electrolyte battery was produced in the same manner as in Example 1 except that, when a positive electrode was produced, the amount of $LiNi_{0.34}Co_{0.33}Mn_{0.33}O_2$ powder was set to 72 mass %, and 18 mass % of $LiFePO_4$ powder was additionally added as a positive electrode-active material, and a charging and discharging cycle test was performed.

Example 11

A nonaqueous electrolyte battery was produced in the same manner as in Example 1 except that, when a positive electrode was produced, as a positive electrode-active material, 72 mass % of $LiAl_{0.15}Mn_{1.85}O_4$ and 18 mass % of $LiCoO_2$ were used in place of $LiNi_{0.34}Co_{0.33}Mn_{0.33}O_2$, and when a charging and discharging treatment and a charging and discharging cycle test were performed, a charging voltage was set to 2.7 V, and a discharging voltage was set to 1.8 V, and a charging and discharging cycle test was performed.

Example 12

A nonaqueous electrolyte battery was produced in the same manner as in Example 1 except that, when a negative electrode was produced, as a negative electrode-active material, monoclinic titanium composite oxide ($TiO_2(B)$) powder was used in place of $Li_4Ti_5O_{12}$ powder, and when a charging and discharging treatment was performed, a charging voltage was set to 2.8 V, and a discharging voltage was set to 1.8 V, and a charging and discharging cycle test was performed.

Example 13

A nonaqueous electrolyte battery was produced in the same manner as in Example 1 except that, when a negative electrode was produced, as a negative electrode-active material, $TiNb_2O_7$ powder was used in place of $Li_4Ti_5O_{12}$ powder, and when a charging and discharging treatment and a charging and discharging cycle test were performed, a charging voltage was set to 2.8 V, and a discharging voltage was set to 1.8 V, and a charging and discharging cycle test was performed.

Example 14

A nonaqueous electrolyte battery was produced in the same manner as in Example 1 except that, when a negative electrode was produced, as a negative electrode-active material, orthorhombic Na-containing niobium titanium complex oxide $Li_2Na_{1.8}Ti_{5.8}Nb_{0.2}O_{14}$ powder was used in place of $Li_4Ti_5O_{12}$ powder, and when a charging and discharging treatment and a charging and discharging cycle test were performed, a charging voltage was set to 3.0 V, and a discharging voltage was set to 1.8 V, and a charging and discharging cycle test was performed.

Example 15

A nonaqueous electrolyte battery was produced in the same manner as in Example 1 except that, when a positive electrode was produced, as a positive electrode-active material, $LiFePO_4$ powder was used in place of $LiNi_{0.34}Co_{0.33}Mn_{0.33}O_2$ powder, when a negative electrode was produced, as a negative electrode-active material, graphite powder was used in place of $Li_4Ti_5O_{12}$ powder, and as a current collector, a copper foil was used in place of an aluminum foil, when a liquid nonaqueous electrolyte was prepared, ethylene carbonate (EC) was used in place of PC, and 1 M of $LiPF_6$ was dissolved in a solvent mixture in which EC and DEC were mixed at a volume ratio of 1:2, and $LiPF_2O_2$ at 1.5 mass % and FEC at 1 mass % with respect to the total amount of the liquid nonaqueous electrolyte were additionally added. Additionally, when a charging and discharging treatment and a charging and discharging cycle test were performed, a charging voltage was set to 3.6 V, and a discharging voltage was set to 2.4 V and a charging and discharging cycle test was performed.

Example 16

A nonaqueous electrolyte battery was produced in the same manner as in Example 15 except that, as a negative electrode-active material, hard carbon powder was used in place of graphite powder, and a charging and discharging cycle test was performed.

Example 17

A nonaqueous electrolyte battery was produced in the same manner as in Example 1 except that, when an aging treatment was performed, the state of charge of the nonaqueous electrolyte battery was changed from 50% to 5%, and a charging and discharging cycle test was performed.

Example 18

A nonaqueous electrolyte battery was produced in the same manner as in Example 1 except that, when an aging treatment was performed, the state of charge of the nonaqueous electrolyte battery was changed from 50% to 80%, and a charging and discharging cycle test was performed.

Example 19

A nonaqueous electrolyte battery was produced in the same manner as in Example 1 except that, when an aging treatment was performed, the state of charge of the nonaqueous electrolyte battery was changed from 50% to 100%, and a charging and discharging cycle test was performed.

Example 20

A nonaqueous electrolyte battery was produced in the same manner as in Example 1 except that a time of an aging treatment was changed from 3 hours to 24 hours, and a charging and discharging cycle test was performed.

Example 21

A nonaqueous electrolyte battery was produced in the same manner as in Example 1 except that conditions for an aging treatment included 3 hours in an environment at 85° C., and a charging and discharging cycle test was performed.

Example 22

A nonaqueous electrolyte battery was produced in the same manner as in Example 1 except that conditions for an aging treatment included 3 hours under an environment at 90° C., and a charging and discharging cycle test was performed.

Example 23

A nonaqueous electrolyte battery was produced in the same manner as in Example 1 except that conditions of an aging treatment included 3 hours under an environment at 95° C., and a charging and discharging cycle test was performed.

Example 24

A nonaqueous electrolyte battery was produced in the same manner as in Example 1 except that, when a liquid nonaqueous electrolyte was prepared, 1.5 mass % of $Li_2PF_3O$ was added to a solvent mixture in place of $LiPF_2O_2$, and a charging and discharging cycle test was performed.

Example 25

A nonaqueous electrolyte battery was produced in the same manner as in Example 1 except that, when a liquid nonaqueous electrolyte was prepared, 1.5 mass % of LiBOB was added to a solvent mixture in place of $LiPF_2O_2$, and a charging and discharging cycle test was performed.

Example 26

A nonaqueous electrolyte battery was produced in the same manner as in Example 1 except that, when a liquid nonaqueous electrolyte was prepared, 1.5 mass % of LiODFB was added to a solvent mixture in place of $LiPF_2O_2$, and a charging and discharging cycle test was performed.

Example 27

A nonaqueous electrolyte battery was produced in the same manner as in Example 1 except that, when a liquid nonaqueous electrolyte was prepared, the amount of $LiPF_2O_2$ added to a solvent mixture was changed from 1.5 mass % to 1.0 mass %, and 1 mass % of TMSB was added to the solvent mixture, and a charging and discharging cycle test was performed.

Example 28

A nonaqueous electrolyte battery was produced in the same manner as in Example 1 except that, when a liquid nonaqueous electrolyte was prepared, the amount of $LiPF_2O_2$ added to a solvent mixture was changed from 1.5 mass % to 1.0 mass %, and 1 mass % of LiODFB was added to the solvent mixture, and a charging and discharging cycle test was performed.

Comparative Example 1

A nonaqueous electrolyte battery was produced in the same manner as in Example 1 except that no aging treatment was performed, and a charging and discharging cycle test was performed.

Comparative Example 2

A nonaqueous electrolyte battery was produced in the same manner as in Example 1 except that, when a liquid nonaqueous electrolyte was prepared, no $LiPF_2O_2$ was added to a solvent mixture, and when an aging treatment was performed, the state of charge of the nonaqueous electrolyte battery was changed from 50% to 100%, and a charging and discharging cycle test was performed.

Comparative Example 3

A nonaqueous electrolyte battery was produced in the same manner as in Example 1 except that, when a liquid nonaqueous electrolyte was prepared, no $LiPF_2O_2$ was added to a solvent mixture, and when an aging treatment was performed, the state of charge of the nonaqueous electrolyte battery was changed from 50% to 100%, and a charging and discharging cycle test was performed.

Comparative Example 4

A nonaqueous electrolyte battery was produced in the same manner as in Example 1 except that, when a liquid nonaqueous electrolyte was prepared, no $LiPF_2O_2$ was added to a solvent mixture, and a time of an aging treatment was changed from 3 hours to 24 hours, and a charging and discharging cycle test was performed.

Comparative Example 5

A nonaqueous electrolyte battery was produced in the same manner as in Example 1 except that, when a positive electrode was produced, as a binding agent, PVdF was used in place of polyacrylonitrile, and a charging and discharging cycle test was performed.

The retention rates of the discharge capacity after the charging and discharging cycle test was performed over 1000 cycles on Examples 1 to 28 and Comparative Examples 1 to 5 are shown in Table 1.

In addition, infrared absorption spectrums of the positive electrode mixture layers of the nonaqueous electrolyte batteries of Examples 1 to 28 and Comparative Examples 1 to 5 after the charging and discharging cycle test was performed were measured according to the ATR method described above. Based on the obtained infrared absorption spectrums, the highest peak intensity $I_1$ in peaks appearing in the wavelength range of 2200 to 2280 $cm^{-1}$, the highest peak intensity $I_2$ in peaks appearing in the wavelength range of 1400 to 1480 $cm^{-1}$, and the highest peak intensity $I_3$ in peaks appearing in the wavelength range of 1650 to 1850 $cm^{-1}$ were measured and $I_2/I_1$ and $I_3/I_2$ were calculated. The results are shown in Table 1. In addition, FIG. 7 shows infrared absorption spectrums of the positive electrode mixture layers of the nonaqueous electrolyte batteries of Example 2 and Comparative Example 2 after the charging and discharging cycle test was performed, which were measured according to the ATR method.

TABLE 1

| | Retention rate after 1000 cycles at 60° C./% | $I_2/I_1$ | $I_3/I_2$ |
|---|---|---|---|
| Example 1 | 89 | 18.1 | 0.3 |
| Example 2 | 85 | 14.0 | 0.3 |
| Example 3 | 84 | 13.5 | 0.5 |
| Example 4 | 81 | 11.9 | 0.6 |
| Example 5 | 93 | 13.7 | 0.4 |
| Example 6 | 97 | 16.3 | 0.1 |
| Example 7 | 91 | 15.2 | 0.3 |
| Example 8 | 88 | 16.4 | 0.3 |
| Example 9 | 82 | 15.1 | 0.4 |
| Example 10 | 89 | 17.0 | 0.2 |
| Example 11 | 90 | 14.4 | 0.5 |
| Example 12 | 85 | 17.2 | 0.3 |
| Example 13 | 84 | 16.9 | 0.4 |
| Example 14 | 86 | 16.6 | 0.4 |
| Example 15 | 80 | 15.8 | 0.8 |
| Example 16 | 83 | 16.0 | 0.7 |
| Example 17 | 90 | 19.5 | 0.3 |
| Example 18 | 87 | 18.0 | 0.4 |
| Example 19 | 87 | 17.5 | 0.4 |
| Example 20 | 89 | 18.1 | 0.4 |
| Example 21 | 85 | 18.2 | 0.5 |
| Example 22 | 83 | 17.8 | 0.6 |
| Example 23 | 82 | 17.2 | 0.8 |
| Example 24 | 80 | 13.9 | 0.5 |
| Example 25 | 86 | 12.6 | 0.4 |
| Example 26 | 88 | 14.7 | 0.3 |
| Example 27 | 87 | 16.5 | 0.3 |
| Example 28 | 90 | 16.8 | 0.2 |
| Comparative Example 1 | 75 | 8.7 | 0.9 |
| Comparative Example 2 | 72 | 6.3 | 0.9 |
| Comparative Example 3 | 69 | 5.8 | 1.3 |
| Comparative Example 4 | 70 | 5.5 | 1.2 |
| Comparative Example 5 | 77 | — | 1.5 |

Figure 7:
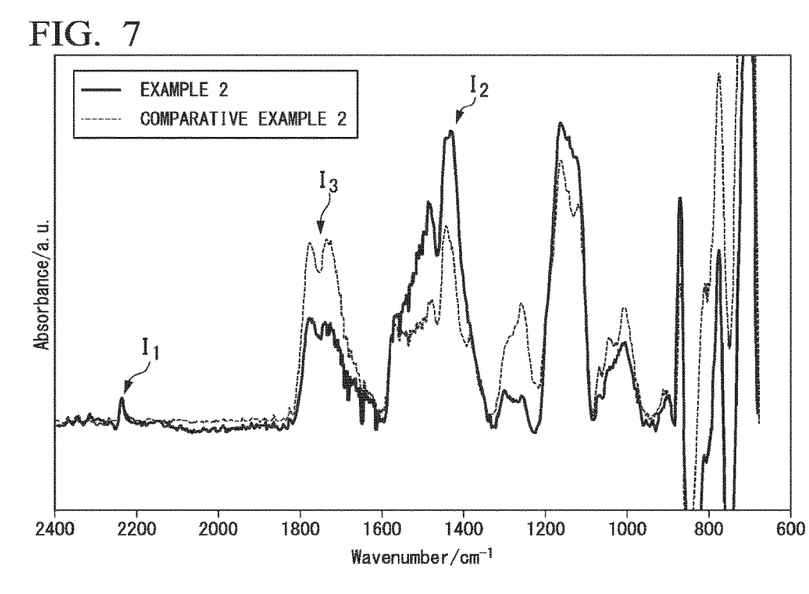
FIG. 7 shows infrared absorption spectrums of positive electrode mixture layers of nonaqueous electrolyte batteries of Example 2 and Comparative Example 2 after a charging and discharging cycle test was performed, which were measured according to an ATR method.

In the infrared absorption spectrums shown in FIG. 7, the peak appearing in the wavelength range of 2200 to 2280 $cm^{-1}$ was a peak derived from a nitrile group of polyacrylonitrile used as the binding agent. Since the amounts of polyacrylonitrile used in Example 2 and Comparative Example 2 were the same, the peak intensity $I_1$ was substantially the same in Example 2 and Comparative Example 2. Therefore, since $I_2/I_1$ in Example 2 was greater than $I_2/I_1$ in Comparative Example 2, it can be understood that the nonaqueous electrolyte battery produced in Example 2 had a larger amount of the inorganic species formed on the surface of the positive electrode mixture layer than the nonaqueous electrolyte battery produced in Comparative Example 2. In addition, since $I_3/I_2$ in Example 2 was smaller than $I_3/I_2$ in Comparative Example 2, it can be understood that the nonaqueous electrolyte battery produced in Example 2 had a smaller amount of the organic species formed on the surface of the positive electrode mixture layer than the nonaqueous electrolyte battery produced in Comparative Example 2.

Comparing Example 1 and Comparative Example 1, it can be understood that, when the aging treatment was performed, since $I_2/I_1$ could be controlled to be 10 or more and 20 or less, and formation of excess organic species was prevented, $I_3/I_2$ could be controlled to be 0.1 or more and 0.8 or less. The capacity retention rate was 75% in Comparative Example 1 in a high-temperature cycle and was 89% in Example 1, and it can be understood that the capacity retention rate in a high-temperature cycle was increased by controlling $I_2/I_1$ and $I_3/I_2$.

According to Examples 2 to 11, it can be understood that it was possible to control $I_2/I_1$ and $I_3/I_2$ when the positive electrode-active material was different or when a plurality of positive electrode-active materials were combined, and life characteristics under a high-temperature environment could be improved by controlling them.

According to Example 12 to 16, it can be understood that, in the nonaqueous electrolyte batteries in which the negative electrode-active material was not limited to $Li_4Ti_5O_{12}$ as in Examples 1 to 11, and various negative electrode-active materials such as a monoclinic titanium composite oxide, $TiNb_2O_7$, an orthorhombic Na-containing niobium titanium complex oxide, graphite, and hard carbon were used, it was possible to form a desired species on the positive electrode and it was possible to obtain a nonaqueous electrolyte battery having excellent high-temperature cycle characteristics.

Examples 17 to 23 show the results obtained when the state of charge, the treatment temperature, and the treatment time of the nonaqueous electrolyte batteries were changed in the aging treatment, and it can be understood that, when the state of charge of the nonaqueous electrolyte battery was set to 5 to 100%, when the treatment temperature was set to 80 to 95° C., and when the treatment was performed at 80° C. for 24 hours, $I_2/I_1$ was 10 or more and 20 or less, and excellent high-temperature cycle characteristics were exhibited.

Examples 24 to 28 show the results of the nonaqueous electrolyte batteries when compounds added to the liquid nonaqueous electrolyte were changed, and it can be understood that $I_2/I_1$ could be controlled when an additive such as $Li_2POF_3$ or LiBOB was used, and excellent high-temperature cycle characteristics were exhibited.

Comparative Examples 2 to 4 show the results obtained when a compound for facilitating formation of a organic and/or inorganic species was not added to the liquid nonaqueous electrolyte and the nonaqueous electrolyte battery was subjected to the aging treatment at a high temperature. It can be understood from the results that $I_2/I_1$ was smaller than 10, formation of the species was insufficient, and high-temperature cycle characteristics deteriorated.

Comparative Example 5 shows the results obtained when only PVdF having no nitrile bond was used as the binding agent of the positive electrode. Since there was no nitrile bond, no $I_1$ was observed, only the result of $I_3/I_2$ is shown in the table, and $I_3/I_2$ was 1.5, and a large amount of the organic species was speculated to be formed. Since high-temperature cycle characteristics deteriorated, it is thought that when a binding agent having a nitrile bond was used for the positive electrode and a desired species was formed, high-temperature cycle characteristics could be improved.

The invention claimed is:

1. A nonaqueous electrolyte battery electrode, comprising:
   a current collector; and
   a mixed layer formed on one surface or both surfaces of the current collector,
   wherein the mixed layer includes an active material and a binding agent, and the ratio $I_2I_1$ of the highest peak intensity $I_2$ in peaks appearing in the wavelength range of 1400 to 1480 $cm^{-1}$ to the highest peak intensity $I_1$ in peaks appearing in the wavelength range of 2200 to 2280 $cm^{-1}$ is 10 or more and 20 or less in an infrared absorption spectrum measured according to a total reflection measurement method.

2. A nonaqueous electrolyte battery electrode, comprising:
   a current collector; and
   a mixed layer formed on one surface or both surfaces of the current collector,
   wherein the mixed layer includes an active material and a binding agent, and the ratio $I_3I_2$ of the highest peak intensity $I_3$ in peaks appearing in the wavelength range of 1650 to 1850 $cm^{-1}$ to the highest peak intensity $I_2$ in peaks appearing in the wavelength range of 1400 to 1480 $cm^{-1}$ is 0.1 or more and 0.8 or less in an infrared absorption spectrum measured according to a total reflection measurement method.

3. The nonaqueous electrolyte battery electrode according to claim 1, wherein the binding agent includes an organic material having a nitrile bond.

4. The nonaqueous electrolyte battery electrode according to claim 1, wherein the active material includes at least one lithium-containing compound selected from the group consisting of a lithium nickel cobalt manganese composite oxide, a lithium manganese composite oxide, a lithium cobalt composite oxide, a lithium iron phosphate, and a lithium manganese iron phosphate.

5. A nonaqueous electrolyte battery, comprising:
   a positive electrode including the nonaqueous electrolyte battery electrode according to claim 1;
   a negative electrode; and
   a nonaqueous electrolyte.

6. A battery pack, comprising the nonaqueous electrolyte battery according to claim 5.

7. The nonaqueous electrolyte battery electrode according to claim 1,
   the mixed layer includes an inorganic coating including an inorganic carbonate material formed on the surface of the mixed layer.

8. The nonaqueous electrolyte battery electrode according to claim 3,
   wherein the organic material having a nitrile bond is polyacrylonitrile.

9. The nonaqueous electrolyte battery electrode according to claim 3,
   further includes at least one selected from the group consisting of polytetrafluoroethylene, polyvinylidene fluoride, fluorine-based rubber, and an acrylic resin of polyacrylic acid and a copolymer thereof.

10. The nonaqueous electrolyte battery electrode according to claim 1,
    wherein the nonaqueous electrolyte battery electrode is positive electrode.

11. A vehicle comprising the battery pack according to claim 6.

12. The nonaqueous electrolyte battery electrode according to claim 2,
    wherein the mixed layer comprises an organic coating and an inorganic coating including an inorganic carbonate material formed on the surface of the mixed layer.

13. The nonaqueous electrolyte battery electrode according to claim 2,
    wherein the binding agent includes an organic material having a nitrile bond.

14. The nonaqueous electrolyte battery electrode according to claim 13, wherein the organic material having a nitrile bond is polyacrylonitrile.

15. The nonaqueous electrolyte battery electrode according to claim 13, further comprising at least one member selected from the group consisting of polytetrafluoroethylene, polyvinylidene fluoride, fluorine-based rubber, an acrylic resin of polyacrylic acid and copolymers thereof.

16. The nonaqueous electrolyte battery electrode according to claim 2,
    wherein the nonaqueous electrolyte battery electrode is a positive electrode.

17. The nonaqueous electrolyte battery electrode according to claim 2,
    wherein the active material comprises at least one lithium-containing compound selected from the group consisting of a lithium nickel cobalt manganese composite oxide, a lithium manganese composite oxide, a lithium cobalt composite oxide, a lithium iron phosphate, and a lithium manganese iron phosphate.

18. A nonaqueous electrolyte battery, comprising:
    a positive electrode comprising the nonaqueous electrolyte battery electrode according to claim 2;
    a negative electrode; and
    a nonaqueous electrolyte.

19. A battery pack, comprising the nonaqueous electrolyte battery according to claim 18.

20. A vehicle comprising the battery pack according to claim 19.

21. The nonaqueous electrolyte battery electrode according to claim 1, wherein the current collector is a positive electrode current collector.

22. The nonaqueous electrolyte battery electrode according to claim 1, wherein the mixed layer is a positive electrode mixture layer.

23. The nonaqueous electrolyte battery electrode according to claim 1, wherein the mixed layer contains an inorganic carbonate material.

24. The nonaqueous electrolyte battery electrode according to claim 2, wherein the current collector is a positive electrode current collector.

25. The nonaqueous electrolyte battery electrode according to claim 2, wherein the mixed layer is a positive electrode mixture layer.

26. The nonaqueous electrolyte battery electrode according to claim 2, wherein the mixed layer contains an inorganic carbonate material.

* * * * *